United States Patent [19]
Rollick et al.

[11] Patent Number: 5,908,546
[45] Date of Patent: *Jun. 1, 1999

[54] DETECTION OF HYDROGEN CHLORIDE

[75] Inventors: Kelly P. Rollick, Pittsburgh; Debra J. Dorisio Deininger, Valencia, both of Pa.

[73] Assignee: Mine Safety Appliances Company, Pittsburgh, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/887,068

[22] Filed: Jul. 2, 1997

[51] Int. Cl.$^6$ .................................................. G01N 27/404
[52] U.S. Cl. ...................... 205/779.5; 204/412; 204/415; 204/432; 205/780; 205/786.5
[58] Field of Search .................................... 204/412, 415, 204/431, 432; 205/778.5, 779, 779.5, 780

[56] References Cited

U.S. PATENT DOCUMENTS

| | | | |
|---|---|---|---|
| 3,239,444 | 3/1966 | Heldenbrand | 204/415 |
| 3,510,420 | 5/1970 | Mills | 204/415 |
| 3,698,955 | 10/1972 | Lilly et al. | 204/426 |
| 4,169,779 | 10/1979 | Tataria et al. | 204/415 |
| 4,302,315 | 11/1981 | Stetter et al. | 204/432 |
| 4,326,927 | 4/1982 | Stetter et al. | 204/432 |
| 4,655,900 | 4/1987 | Neti et al. | 204/415 |
| 4,960,496 | 10/1990 | Hoke | 205/779.5 |
| 5,202,011 | 4/1993 | Kiesele et al. | 204/415 |
| 5,316,648 | 5/1994 | Kuhn et al. | 204/415 |
| 5,624,546 | 4/1997 | Milco | 205/779.5 |

FOREIGN PATENT DOCUMENTS

| | | |
|---|---|---|
| 778965 | 8/1972 | Belgium . |
| 0 532 932 | 3/1993 | European Pat. Off. . |
| 2 388 273 | 11/1978 | France . |
| 93 21522 | 10/1993 | WIPO . |
| 96 33404 | 10/1996 | WIPO . |

*Primary Examiner*—T. Tung
*Attorney, Agent, or Firm*—James G. Uber; Henry E. Bartony, Jr.

[57] ABSTRACT

The present invention provides an electrochemical sensor for the detection of hydrogen chloride. In general, the electrochemical sensor comprises a housing having disposed therein a working electrode, a reference electrode and a counter electrode. The electrochemically active surface of the working electrode preferably comprises a gold film having a thickness of approximately 1000 to 3000 Å. Electrical connection is maintained between the working electrode and the counter electrode via an electrolyte present within the housing. The electrochemical gas sensor preferably further comprises circuitry for maintaining the working electrode at a potential in the range of approximately 1025 to approximately 1400 mV versus the normal hydrogen electrode. The present invention also provides a method of using such a sensor to detect hydrogen chloride.

13 Claims, 7 Drawing Sheets

DETECTION OF HYDROGEN CHLORIDE

FIELD OF THE INVENTION

The present invention relates to an electrochemical sensor, and particularly, to an electrochemical sensor for detecting hydrogen chloride.

BACKGROUND OF THE INVENTION

In an electrochemical gas sensor, the gas to be measured typically passes from the atmosphere into the sensor housing through a gas porous or gas permeable membrane to a working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working and counter electrodes. A comprehensive discussion of electrochemical gas sensors is provided in Cao, Z. and Stetter, J. R., "The Properties and Applications of Amperometric Gas Sensors," *Electroanalysis*, 4(3), 253 (1992), the disclosure of which is incorporated herein by reference.

To be useful as an electrochemical sensor, a working and counter electrode combination must be capable of producing an electrical signal that is (1) related to the concentration of the analyte and (2) sufficiently strong to provide a signal-to-noise ratio suitable to distinguish between concentration levels of the analyte over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte and carry the lowest possible current to maintain a constant potential.

Electrical connection between the working electrode and the counter electrode is maintained through an electrolyte. The primary functions of the electrolyte are: (1) to efficiently carry the ionic current; (2) to solubilize the analyte gas; (3) to support both the counter and the working electrode reactions; and (4) to form a stable reference potential with the reference electrode. The primary criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical cell provide a surface at which an oxidation or a reduction reaction occurs to provide a mechanism whereby the ionic conduction of the electrolyte solution is coupled with the electron conduction of the electrode to provide a complete circuit for a current.

The measurable current arising from the cell reactions because of the analyte in the electrochemical cell is directly proportional to the rate of reaction. Preferably, therefore, a high reaction rate is maintained in the electrochemical cell. For this reason, the counter electrode and/or the working electrode of the electrochemical cell generally comprise an appropriate electrocatalyst on the surface thereof to enhance the reaction rate. If the reaction rate of either half cell reaction is impeded, resulting in a low exchange current density, the equilibrium current of the electrochemical cell may be easily perturbed during measurement. Such deviation can result in undesirable side reactions and/or nonlinear behavior over the range of analyte concentrations desired to be detected.

The type, rate, and efficiency of the chemical reactions within an electrochemical gas sensor are controlled, in significant part, by the material(s) used to make the working electrode and counter electrode. Indeed, extensive research efforts are expended to develop improved working electrodes, counter electrodes and electrochemical systems generally. See Cao, supra.

In the case of electrochemical sensors for the detection of hydrogen chloride (HCl), these efforts have met with somewhat limited success. In that regard, currently available electrochemical sensors for the detection of HCl suffer from a number of significant drawbacks, including: (1) poor response time; (2) short service time; (3) sensitivity to changes in temperature; (4) sensitivity to changes in humidity; and (5) susceptibility to interference from or cross-sensitivity to gases other than HCl (for example, hydrogen sulfide ($H_2S$)).

It is desirable, therefore, to develop new electrochemical sensors and electrodes for use in such electrochemical sensors for the detection of hydrogen chloride which mitigate or substantially eliminate one or more of the above drawbacks.

SUMMARY OF THE INVENTION

The present invention provides an electrochemical sensor for the detection of hydrogen chloride. In general, the electrochemical sensor preferably comprises a housing having disposed therein a working electrode, a reference electrode and a counter electrode. The electrochemically active surface of the working electrode preferably comprises a gold film having a thickness of approximately 1000 to 3000 Å. Electrical connection is maintained between the working electrode and the counter electrode via an electrolyte present within the housing. The electrochemical gas sensor preferably further comprises circuitry for maintaining the working electrode at a potential in the range of approximately 1025 mV to approximately 1400 mV versus the normal hydrogen electrode (that is, the operating potential is preferable in the range of approximately +1050 mV to approximately +1400 mV relative to the normal hydrogen electrode). More preferably, the working electrode is maintained at a potential in the range of approximately 1050 mV to approximately 1350 mV versus the normal hydrogen electrode. Most preferably, the working electrode is maintained as a potential in the range of approximately 1100 mV to approximately 1200 mV versus the normal hydrogen electrode.

Preferably, the working electrode comprises a film of gold sputter coated over a porous, water-resistant membrane, such as a GoreTex® membrane. The electrochemically active surface of the counter electrode preferably comprises platinum. Similarly, the electrochemically active surface of the reference electrode preferably comprises platinum.

The present invention also provides a method of using an electrochemical gas sensor comprising a working electrode having an electrochemically active surface comprising a gold film of a thickness of approximately 1000 Å to 3000 Å for the detection of hydrogen chloride. The method preferably comprises the steps of:

a. placing the electrochemical gas sensor in communicative connection with an environment containing hydrogen chloride such that hydrogen chloride can react at the working electrode;

b. measuring the current flow between the working electrode and the counter electrode to obtain a measurement of the concentration of hydrogen chloride in the environment.

The method preferably further comprises the step of:

c. maintaining the working electrode at a potential in the range of approximately 1025 to approximately 1400 mV versus the normal hydrogen electrode.

DETAILED DESCRIPTION OF THE INVENTION

Figure 1:
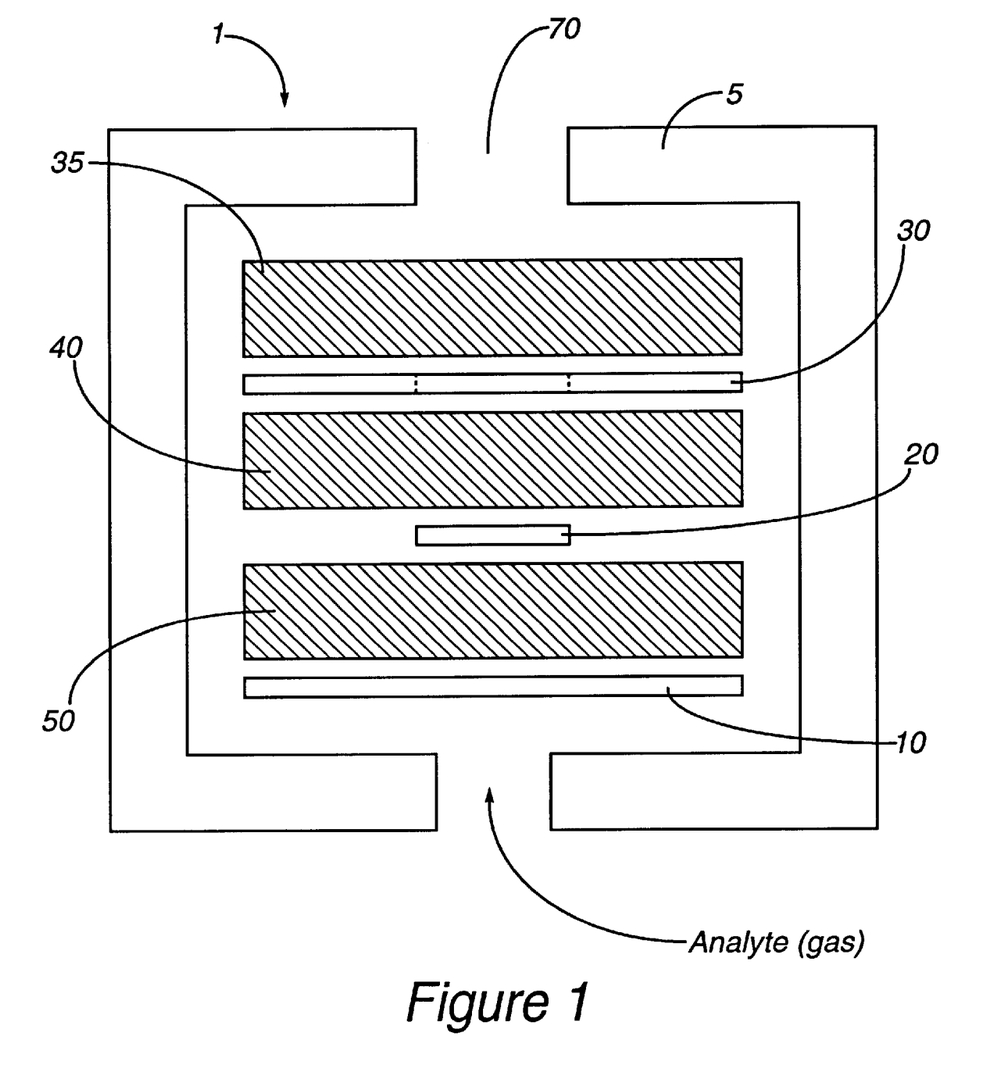
FIG. 1 is a simplified schematic representation of a cross-sectional view of an embodiment of an electrochemical gas sensor of the present invention.

As illustrated in FIG. 1, electrochemical hydrogen chloride sensor 1 preferably comprises a housing 5, enclosing a working electrode 10, a reference electrode 20 and a counter electrode 30. In fabricating electrochemical hydrogen chloride sensors 1 for use in the present studies a porous spacer or wick 35 was first placed within housing 5. Counter electrode 30 was then placed into housing 5. A porous spacer or wick 40 was preferably then placed within housing 5 followed by reference electrode 20. A porous wick 50 was subsequently placed within housing 5 followed by working electrode 10.

After placement of working electrode 10 within housing 5, the perimeter of working electrode 10 was heat sealed to housing 5. The interior of housing 5 was then filled with an electrolyte such as sulfuric acid ($H_2SO_4$) via opening 70. Upon filling of the interior of housing 5 with electrolyte, opening 70 was sealed, preferably via heat sealing using a water resistant membrane such as a GoreTex® film (not shown). A detailed discussion of a preferred assembly, including connection of electrical leads, for electrochemical gas sensor 1 is set forth in U.S. Pat. No. 5,338,429, the disclosure of which is incorporated herein by reference.

Wicks 40 and 50 operate to prevent physical contact of the electrodes but allow the liquid electrolyte to contact the electrodes and thereby provide ionic connection between working electrode 10 and counter electrode 30. Preferably, the electrolyte used in electrochemical hydrogen chloride sensor 1 is sulfuric acid.

The electrochemically active surface of working electrode 10 preferably comprises gold (Au). Working electrodes 10 for use in electrochemical sensors 1 for the present studies were preferably fabricated via sputtering deposition of gold upon a gas porous, water resistant membrane such as Gore-Tex film as known in the, art. Thin films of gold can also be deposited upon a GoreTex film using other methods such as evaporative vapor deposition. As known in the art, GoreTex films provide a very good support for an electrochemically active material and also provide a good gas porous diffusion barrier, allowing the analyte gas to diffuse into the electrochemical sensor while preventing the escape of liquid electrolyte. The gold layer is preferably deposited as a relatively thin film so that permeability is maintained, but not so thin as to result in isolated islands of gold and associated high resistance. In that regard, the gold is preferably sputtered to a thickness of approximately 1000 Å to 3000 Å. More preferably, the gold is sputtered to a thickness of approximately 1900 to 2800 Å. Such thin films also provide improved response times.

Counter electrodes 30 and reference electrodes 20 for use in electrochemical sensors 1 for the present studies may be fabricated via silk screen deposition of an ink comprising a suitable electrochemically active material. In general, the electrochemically active material used in counter electrodes 30 and reference electrodes 20 is not critical to the operation of electrochemical sensor 1. The ink may deposited via silk screening upon a GoreTex film as known in the art. The ink may also be deposited using hand painting techniques as known in the art. Preferably, a film of electrochemically active material having a thickness in the range of approximately 1 to 10 mil is deposited. The support for the film can comprise other electrically conductive materials such as, for example, electrically conductive carbon.

The electrochemically active surfaces of counter electrode 30 and reference electrode 20 preferably comprise platinum (Pt). In the case of platinum, counter electrodes 30 and reference electrodes 20 for the present studies were preferably fabricated via hand painting deposition of an ink comprising platinum powder upon a GoreTex film.

After deposition of the films upon counter electrode 30 and reference electrode 20 as described above, the films were preferably sintered to fix the electrochemically active material upon the substrate GoreTex such as is described in U.S. Pat. No. 4,790,925, the disclosure of which is incorporated herein by reference.

Figure 2:
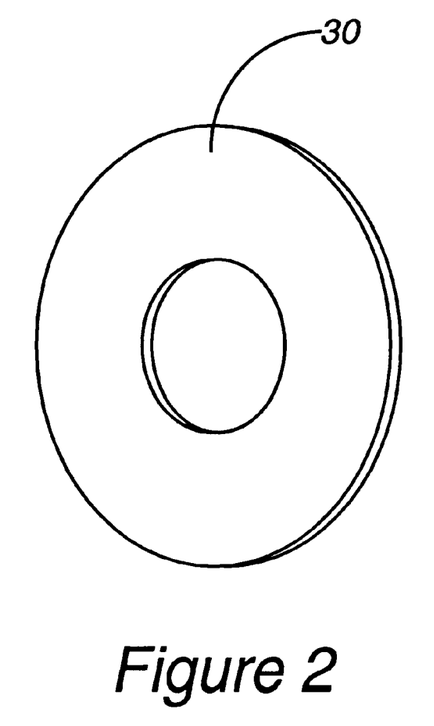
FIG. 2 is a perspective view of an embodiment of the present counter electrode.
Figure 3:
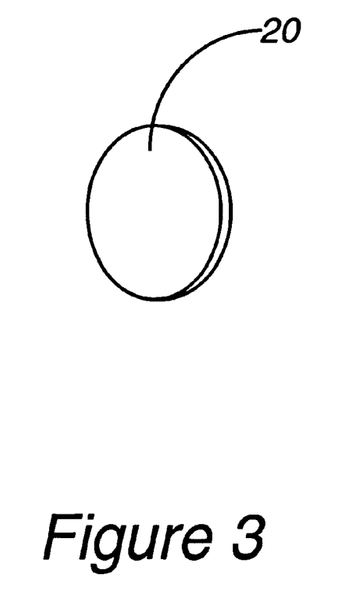
FIG. 3 is a perspective view of an embodiment of the present reference electrode.

As illustrated in FIGS. 1 and 2, counter electrode 30 is preferably shaped in the general form of an annulus or ring. As illustrated in FIGS. 1 and 3, reference electrode 20 is preferably shaped in a generally circular form (that is, in the general shape of a disk). As clear to those skilled in the art, however, counter electrode 30, reference electrode 20 and working electrode 10 of electrochemical sensor 1 can be fabricated in many different shapes.

Preferably, electrochemical hydrogen chloride sensor 1 is subjected to a "cook-down" or "equilibration" period before use thereof to provide an adequately stable and low baseline.

During the cook-down or equilibration period, electrochemical sensor 1 is stored at ambient conditions for a defined period of time. As common in the art, electrochemical sensor 1 is preferably maintained at operating potential during the cook-down period. The operating potential of the electrochemical sensor 1 is preferably +1025 mV to approximately +1400 mV versus the normal hydrogen electrode (or approximately +25 mV to approximately +400 mV versus the platinum/air reference electrode). Most preferably, the operating potential of the electrochemical sensor 1 is preferably +1100 mV to +1200 mV versus the normal hydrogen electrode. For the present studies, working electrode 10 was preferably maintained at a potential of 1200 mV versus the normal hydrogen electrode during the cook-down period.

Preferably, a substantially stable baseline in the range of approximately −0.25 $\mu$A to approximately +0.25 $\mu$A is achieved during the cook-down period. It has been found that a cook-down period of approximately one hour is sufficient to provide an adequate baseline for electrochemical hydrogen chloride sensor 1. Briefer cook-down periods have not yet been investigated, however. Electrochemical hydrogen chloride sensors 1 used in the studies discussed below were subjected to a one hour cook-down period.

Response time is an empirical measure of the speed of response of a sensor and is critically dependent on the manner in which the test is performed (for example, the length of time the experiment lasts and/or the time at which the sensor reaches 100% of its final output). In the present studies, the response time was based upon a ten (10) minute exposure to test gas. Response time was generally tabulated as the 90% response time ($t_{90}$) unless otherwise indicated. The $t_{90}$ response time is the time, in seconds, required for the sensor to reach 90% of the response or output obtained after ten minutes of exposure to test gas. The sensitivity (in units of $\mu$A/ppm HCl) was established as the sensor output after ten (10) minutes of exposure to hydrogen chloride.

The present studies included linear and cyclic voltammetries performed using an EG&G model 263A potentiostat controlled by Model 270/250 Research Electrochemistry software also produced by EG&G. This software controlled both the applied potential and the data acquisition in cyclic studies. Further studies at single potentials were done using a BAS Voltammograph to apply a fixed potential. Data was recorded with a strip chart recorder or a Fluke digital multimeter. Sensor response in $\mu$A and response time (reported as $t_{90}$) were determined from the strip charts as known in the art.

All the sensor cells in the studies had a single 0.230 inch diameter inlet hole to allow the test gas to enter the sensor cells. An average output of approximately 0.30 $\mu$A/ppm was obtained under these experimental conditions. As clear to one of ordinary skill in the art, sensitivity can generally be increased by increasing the total surface area of such inlet holes to allow more gas to enter the sensor cell. The signal/noise ratio of electrochemical sensors of the present invention was found to be larger than provided by previous electrochemical sensors for the detection of hydrogen chloride. The electrochemical sensors of the present invention were found to provide a signal/noise ratio suitable to measure concentrations of hydrogen chloride at least as low as 0.1 ppm. Prior electrochemical sensors for the detection of hydrogen chloride typically cannot resolve concentrations lower than 0.5 ppm.

The electrochemical sensors of the present invention were found to provide a substantially linear signal over at least the range of approximately 0 to 50 ppm hydrogen chloride. Concentration higher than 50 ppm were not studied, however. This response time of the present sensors was found to be less than approximately 50 seconds to 90%. The response time is approximately twice as fast as possible with previous electrochemical sensors for the detection of hydrogen chloride. The $t_{90}$ was found to be substantially constant over the life of the sensor.

As typical of sensors comprising aqueous electrolytes, the sensitivity of the sensors of the present invention was found to be affected by humidity. Sensitivity was found to decrease if the sensor was stored in low humidity, whereas sensitivity was found to increase if the sensor was stored in a humid environment. In general, sensitivity was found to decrease if the sensors were stored in an environment having a relative humidity of less than approximately 15%. Preferably, therefore, the sensors of the present invention are stored in an environment having a relative humidity in the range of approximately 15 to 90%. It is believed that the drop in sensor sensitivity at low humidity is a result of loss of solution contact. This "drying" and the resultant sensitivity loss at low humidity are reversible upon exposure of the sensor to ambient conditions in which the relative humidity is preferably in the range of approximately 15 to 90%.

Unlike currently available sensors for the detection of hydrogen chloride, however, the sensors of the present invention were found to be relatively insensitive to short term changes in humidity. In that regard, previous hydrogen chloride sensors exhibit an immediate change in sensor output as a result of changes in humidity.

Similarly, the sensors of the present invention were found to be relatively insensitive to short term changes in temperature, whereas previous hydrogen chloride sensors exhibit an immediate change in sensor output as a result of changes in temperature. Table 1 sets forth a comparison of the output of an electrochemical sensor of the present invention and the output of a CiTicel 7HL hydrogen 5 chloride sensor available from City Technology of Portsmouth, England at various temperature. As illustrated by the data of Table 1, the output of the electrochemical sensor of the present invention is less sensitive to changes in temperature than is the output of the City Technology 10 sensor. The sample gas in the studies of Table 1 was 40 ppm HCl in nitrogen.

TABLE 1

| Temperature | Present Electrochemical Sensor (ppm) | CiTicel 7HL Electrochemical Sensor (ppm) |
|---|---|---|
| 25° C. | | |
| Zero | 0 | 0 |
| Span | 40 | 40 |
| 40° C. | | |
| Zero | 0 | 4 |
| Span | 39 | 42 |
| 0° C. | | |
| Zero | 0 | −3 |
| Span | 39 | 31 |

The results of several interferent studies are set forth in Table 2. The data provided for each interferent gas correspond to the sensor output (that is, the indicated concentration of hydrogen chloride in ppm) upon exposure of the sensor to the indicated amount (set forth in ppm) of the interferent gas. The results indicate that the present sensor is less susceptible to erroneous results arising from the presence of the interferent gases studied than previous hydrogen chloride sensors.

TABLE 2

| Sample | 40 ppm HCl | 2 ppm Cl$_2$ | 10 ppm H$_2$S | 10 ppm SO$_2$ |
|---|---|---|---|---|
| Sensor Response (ppm HCl indicated) | 40 | 0 | 15 | 0 |

Figure 4:
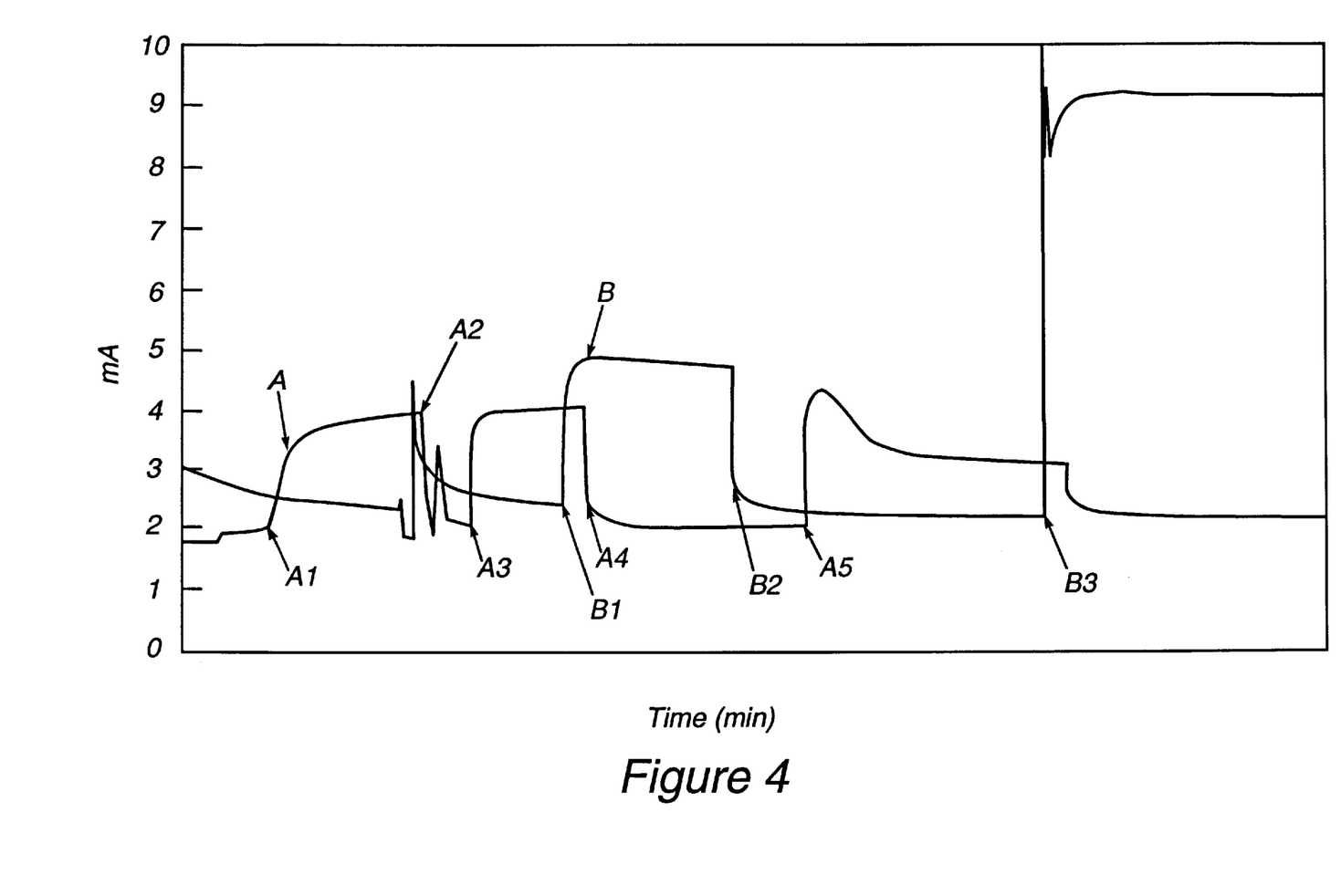
FIG. 4 is a graph of an interferent study comparing the output of a sensor of the present invention with the output of a hydrogen chloride sensor having a working electrode fabricated with gold powder in the presence of hydrogen chloride and the interferent hydrogen sulfide.

FIG. 4 illustrates the output of an electrochemical sensor of the present invention (line A) as compared to the output of an electrochemical sensor comprising a working electrode fabricated from relatively "low" specific surface area powdered gold (0.18 to 0.34 m$^2$/g) (line B) in the presence of hydrogen chloride and hydrogen sulfide at an operating potential of +1200 mV versus the normal hydrogen electrode.

As represented by line A, an electrochemical sensor having a working electrode comprising a sputter coated gold film was exposed to a sample gas. At time A1 a concentration of approximately 42 ppm hydrogen chloride was introduced into the sample gas. The hydrogen chloride supply was discontinued at time A2. A concentration of approximately 42 ppm hydrogen chloride was once again introduced into the sample gas at time A3 and was discontinued at time A4. The somewhat slow response time observed after time A1 is believed to be a result of lag time in the supply of hydrogen chloride as the hydrogen chloride cylinder was turned off between experiments to conserve gas. At time A5, a concentration of approximately 42 ppm hydrogen sulfide was introduced into the sample gas.

As represented by line B, an electrochemical sensor having a working electrode comprising low specific surface area powdered gold (0.18 to 0.34 m$^2$/g) was exposed to a sample gas. At time B1 a concentration of approximately 42 ppm hydrogen chloride was introduced into the sample gas. The hydrogen chloride supply was discontinued at time B2. At time B3, a concentration of approximately 42 ppm hydrogen sulfide was introduced into the sample gas. At time B3, the scale of the graph of FIG. 4 changes from a full scale of approximately 0.05 mA to a full scale of approximately 0.1 mA.

Figure 5A:
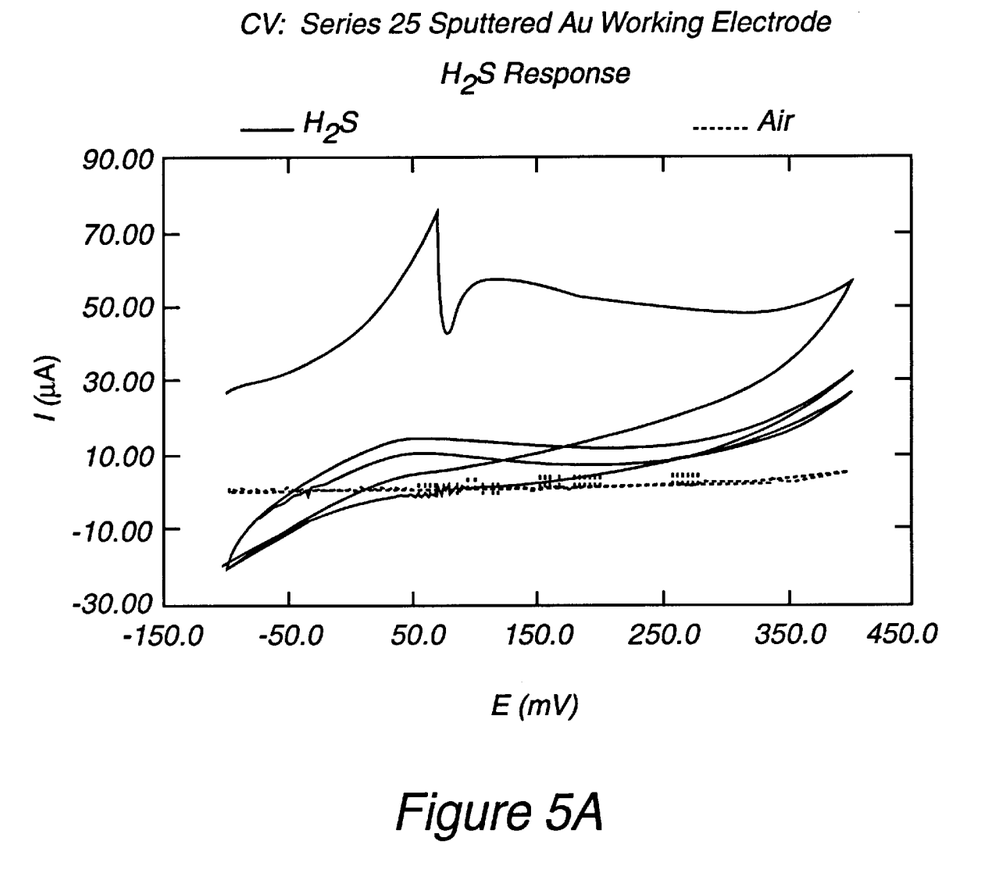
FIG. 5A plots a study of the output of an electrochemical sensor of the present invention as a function of cycling operating potential in the presence of the interferent hydrogen sulfide.
Figure 5B:
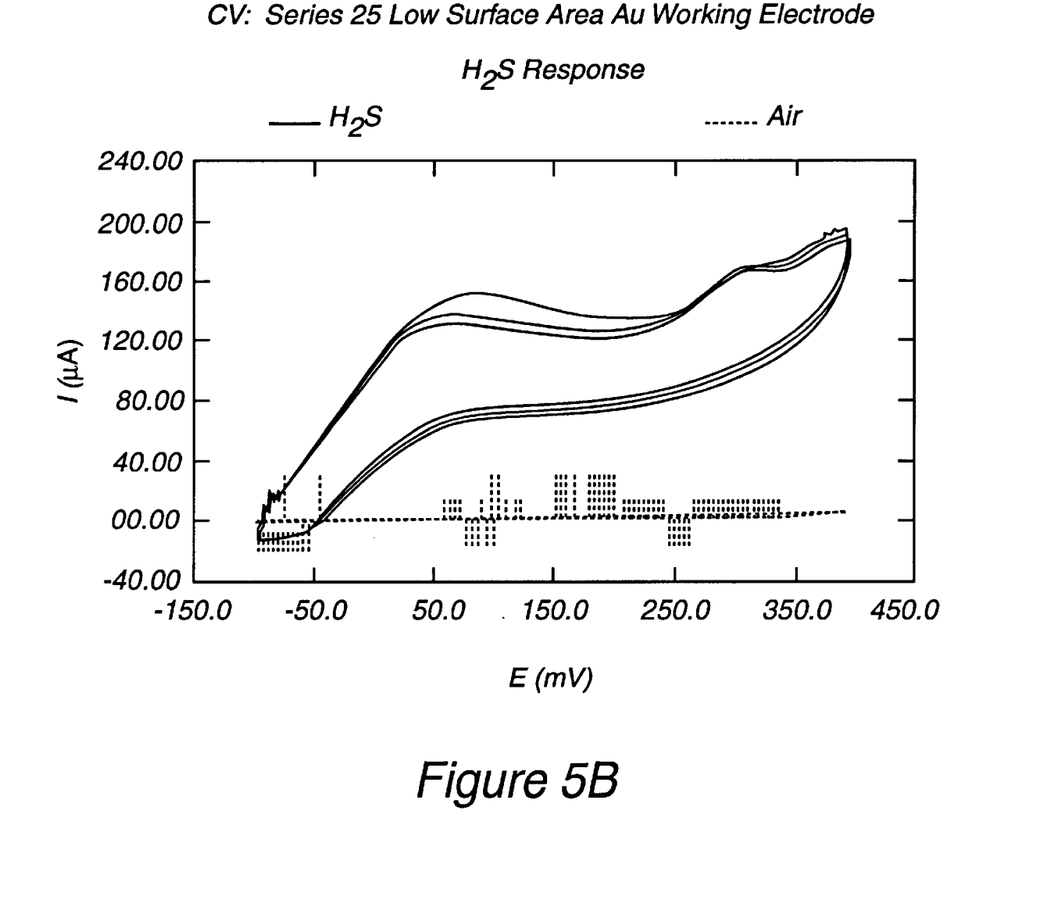
FIG. 5B plots a study of the output of an electrochemical sensor having an electrode fabricated from relatively low surface area powdered gold as a function of cycling operating potential in the presence of the interferent hydrogen sulfide.
Figure 6A:
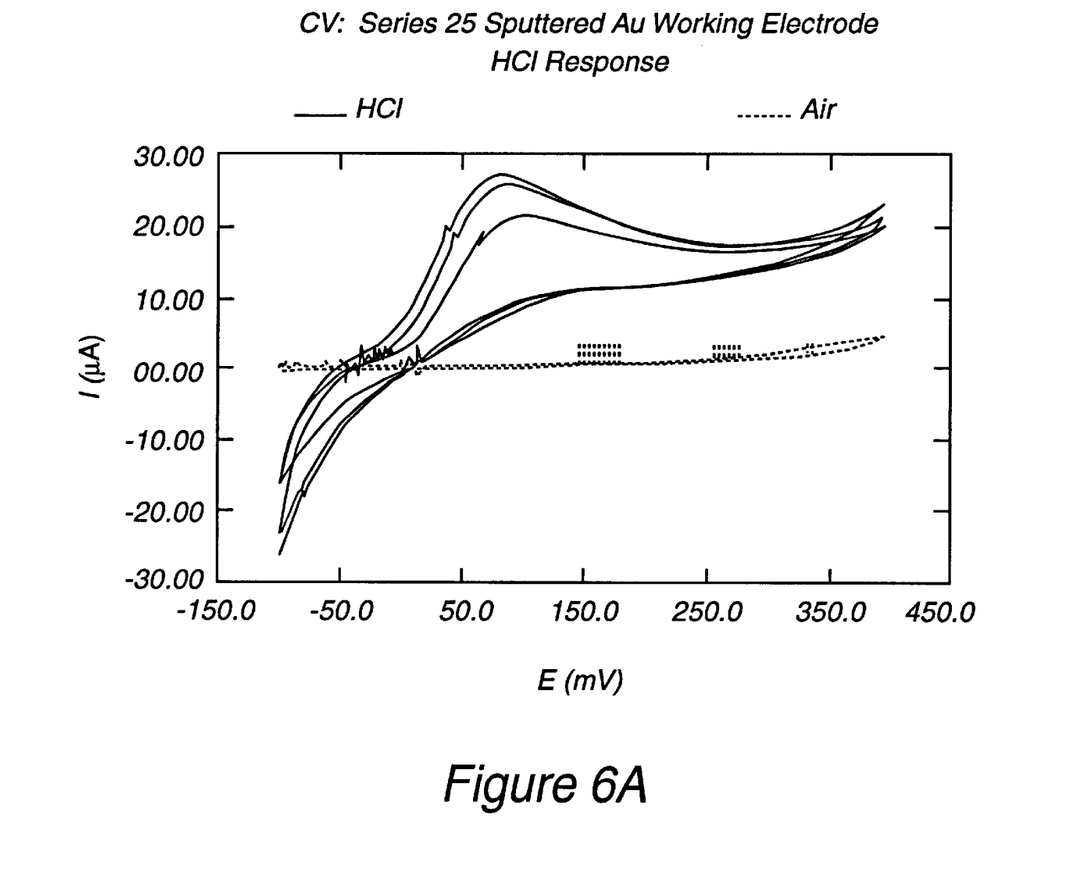
FIG. 6A plots a study of the output of an electrochemical sensor of the present invention as a function of cycling operating potential in the presence of the analyte hydrogen chloride.
Figure 6B:
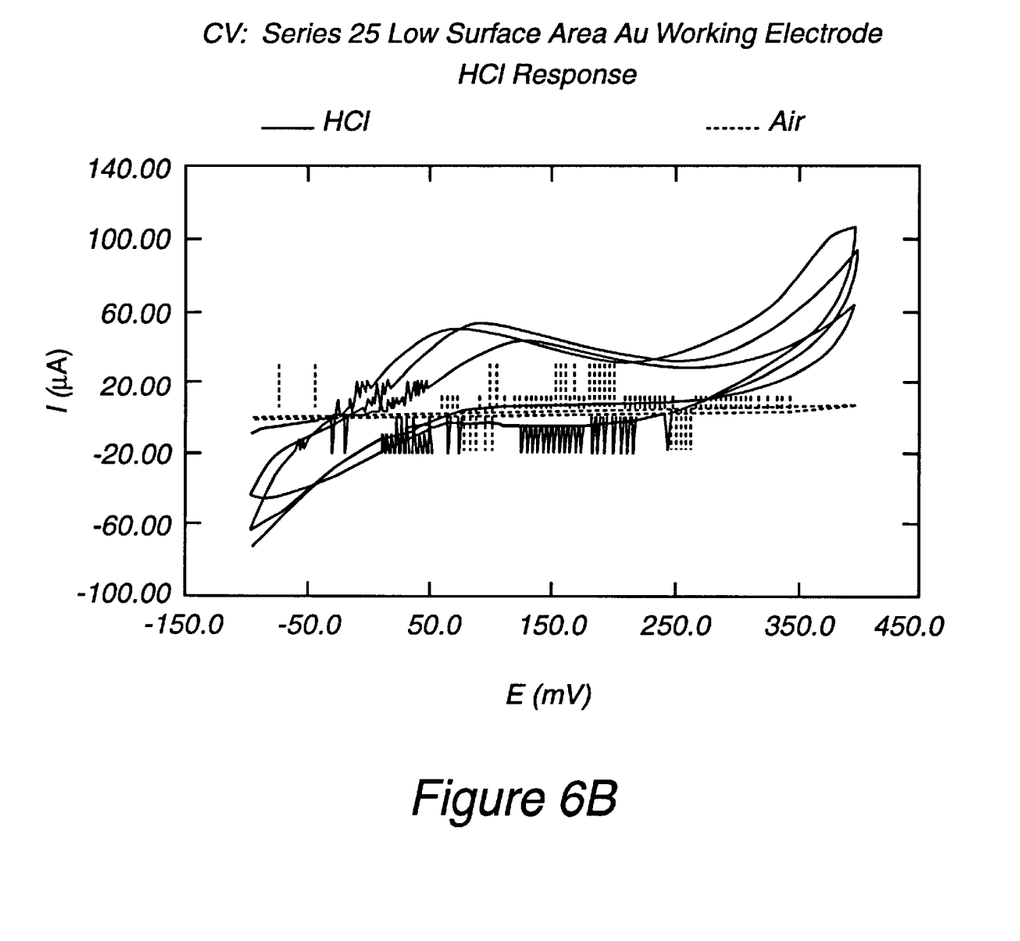
FIG. 6B plots a study of the output of an electrochemical sensor having an electrode fabricated from relatively low surface area powdered gold as a function of cycling operating potential in the presence of the interferent hydrogen chloride.

FIGS. 5A illustrates the output of an electrochemical sensor of the present invention as a function of cycling operating potential in the presence of hydrogen sulfide. For comparison, FIG. 5B illustrates the output of an electrochemical sensor comprising a working electrode fabricated from relatively "low" specific surface area powdered gold (0.18 to 0.34 m$^2$/g) as a function of cycling operating potential in the presence of hydrogen sulfide. In the studies of FIGS. 5A and 5B, the operating potential of the sensor was cycled from −1100 to +1400 mV (versus the NHE) and back to −1100 mV at a rate of 0.5 mV per second. The cycle was repeated three time continuously with approximately 40 ppm of hydrogen sulfide gas applied. FIGS. 6A and 6B, illustrate similar studies with a sputtered gold working electrode and a low specific surface area powdered gold (0.18 to 0.34 m $^2$/g) working electrode, respectively, in the presence of hydrogen chloride.

The present inventors have found that, unlike typical working electrodes, a working electrode comprising a relatively thin film of gold (see FIG. 4 and FIG. 5A) relatively quickly loses much of its sensitivity to hydrogen sulfide. Indeed, comparing FIGS. 5A and 5B, it is seen that the response to hydrogen sulfide is substantially reduced after the first cycle in the case of a working electrode comprising a sputtered film of gold, while the response to hydrogen sulfide of a working electrode comprising low surface area gold is unaffected by previous exposure to hydrogen sulfide at the levels of the study over the course of the study. It is believed that application of hydrogen sulfide to such an electrode at the operating potentials of the present invention poisons the electrode against further detection of hydrogen sulfide. The sensitivity of the working electrode to hydrogen chloride remains relatively unchanged, however. This result is not observed with working electrodes fabricated from powdered gold using typical fabrication techniques.

After poisoning as described above, the cross sensitivity of the sensors of the present invention to the presence of hydrogen sulfide is generally found to be less than or equal to approximately 1:1 (that is, 1 ppm of hydrogen chloride is indicated for each 1 ppm of hydrogen sulfide present in the test sample). The data set forth in Table 2 is for a sensor that has not undergone such a hydrogen sulfide poisoning procedure. The cross sensitivity of previous hydrogen chloride sensors to hydrogen sulfide is generally found to be approximately to 2:1 (that is, 2 ppm of hydrogen chloride is indicated for each 1 ppm of hydrogen sulfide present in the test sample).

The surface area of a working electrode fabricated to have a thin film of gold thereon is in the range of approximately two to three times the actual area of the electrode. The surface of a working electrode fabricated using standard silk screen or hand painting techniques with even relatively low-specific-surface-area powdered gold is in the range of approximately 50 to 100 times the actual area of the electrode. It is believed that in the case of a working electrode comprising a relatively thin film of gold the sulfur of hydrogen sulfide bonds to the gold and prevents further reaction of hydrogen sulfide. This bonding, however, does not substantially affect the reaction of hydrogen chloride at the working electrode. This effect is not observed in the case of high surface area electrodes.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of using an electrochemical gas sensor for the detection of hydrogen chloride, the electrochemical gas sensor comprising a working electrode, a reference electrode, a counter electrode, and an electrolyte, all contained within a housing, the electrochemically active surface of the working electrode comprising a gold film having a thickness in the range of approximately 1000 Å to approximately 3000 Å, the method comprising the steps of:

a. placing the electrochemical gas sensor in communicative connection with an environment containing hydrogen chloride such that hydrogen chloride can react at the working electrode;

b. measuring the current flow between the working electrode and the counter electrode to obtain a measurement of the concentration of hydrogen chloride in the environment.

2. The method of claim 1 further comprising the step of:

c. maintaining the working electrode at a potential in the range of approximately 1025 mV to approximately 1400 mV versus the normal hydrogen electrode.

3. The method of claim 2 wherein the working electrode is maintained at a potential in the range of approximately 1050 mV to approximately 1350 mV versus the normal hydrogen electrode.

4. The method of claim 2 wherein the working electrode is maintained at a potential in the range of approximately 1100 mV to approximately 1200 mV versus the normal hydrogen electrode.

5. The method of claim 2 wherein the thickness of the gold film is in the range of approximately 1900 Å to approximately 2800 Å.

6. The method of claim 1 wherein the gold film is sputter coated over a porous membrane.

7. The method of claim 1 wherein the electrochemically active surface of the counter electrode comprises platinum.

8. The method of claim 1 wherein the electrochemically active surface of the reference electrode comprises platinum.

9. The method of claim 1 wherein the electrochemically active surfaces of the reference electrode and the counter electrode comprise platinum.

10. The method of claim 1 wherein the electrolyte comprises sulfuric acid.

11. The method of claim 1 wherein the thickness of the gold film is in the range of approximately 1900 Å to approximately 2800 Å.

12. The method of claim 1, further comprising the step of:

c. before placing the electrochemical gas sensor in communicative connection with an environment containing hydrogen chloride, exposing the working electrode to an atmosphere containing hydrogen sulfide of a sufficient concentration for a sufficient length of time to substantially decrease a sensitivity of the working electrode to hydrogen sulfide.

13. The method of claim 12 wherein the sensitivity of the working electrode to hydrogen sulfide is decreased by at least approximately 50 percent.

* * * * *